United States Patent [19]
Petersen

[11] Patent Number: 5,955,122
[45] Date of Patent: *Sep. 21, 1999

[54] METHOD OF IMPROVING EFFICIENCY IN RUMINANTS

[75] Inventor: Mark K. Petersen, Las Cruces, N.Mex.

[73] Assignee: New Mexico State University Technology Transfer Corporation, Las Cruces, N.Mex.

[ * ] Notice: This patent is subject to a terminal disclaimer.

[21] Appl. No.: 08/938,140

[22] Filed: Sep. 26, 1997

Related U.S. Application Data

[62] Division of application No. 08/516,252, Aug. 17, 1995, Pat. No. 5,672,366, which is a continuation of application No. 08/087,493, Jul. 6, 1993, abandoned.

[51] Int. Cl.$^6$ .................................................. A23K 1/18
[52] U.S. Cl. ................................................ 426/2; 426/807
[58] Field of Search ........................................ 426/2, 807

[56] References Cited

U.S. PATENT DOCUMENTS

| | | | |
|---|---|---|---|
| 2,597,566 | 5/1952 | Chiego | 260/123.7 |
| 2,702,245 | 2/1955 | Mayer | 99/2 |
| 2,958,600 | 11/1960 | Thurman | 99/2 |
| 3,249,441 | 5/1966 | Reynolds et al. | 99/2 |
| 3,416,928 | 12/1968 | Freese | 99/2 |
| 3,959,493 | 5/1976 | Baalsrud et al. | 426/2 |
| 4,013,762 | 3/1977 | Benson et al. | 424/242 |
| 4,138,505 | 2/1979 | Hart et al. | 426/573 |
| 4,225,620 | 9/1980 | Rawlings et al. | 426/2 |
| 4,269,865 | 5/1981 | Retrum | 426/657 |
| 4,292,334 | 9/1981 | Nishizawa et al. | 426/447 |
| 4,690,951 | 9/1987 | Anderson et al. | 514/653 |
| 4,937,077 | 6/1990 | Deetz, III | 426/442 |
| 5,004,728 | 4/1991 | Chalupa et al. | 514/12 |
| 5,089,287 | 2/1992 | Michaelson | 426/647 |
| 5,114,708 | 5/1992 | Hunter et al. | 514/716 |
| 5,182,126 | 1/1993 | Vinci et al. | 426/74 |
| 5,660,852 | 8/1997 | McKeown et al. | 424/438 |
| 5,662,958 | 9/1997 | Kennelly et al. | 426/630 |

OTHER PUBLICATIONS

Wiley et al., J. Anim. Sci., vol. 69, p. 4279–4293, 1991.
National Research Council; Ruminant Nitrogen Usage, p. 32–33, 1985.
National Research Council; Nutrient Requirements of Sheep, Sixth Edition, Chap 2, pp. 2–11, 45–47, 1985.
Beam, S.W., et al., "Effect of Insulin Administration During Follicular Growth on Serum Glucose and Hormone Profiles in Ewe Lambs," *Can. J. Anim. Sci., Jun.* 1992, 421–426, vol. 72.
Bellows, R.A., et al., "Exploratory Studies of the Effects of Insulin and Gonadotropin (PMS) on Ovarian Activity in Beef Heifers," *Proc. West. Sec. Amer. Soc. Anim. Sci.,* 1964, VII–V16, vol. 15.
Chang, C.J. et al, "Changes of Mammary Vein Concentrations of Glucose and Free Fatty Acids Induced by Exogenous Insulin and Glucose, and Relation to Mammary Gland Function in Saanen Goats," *Small Ruminant Res.,* 1992, 123–133, vol. 7.
Cox, N.M., et al., "Enhancement of Ovulation Rate in Gilts by Increasing Dietary Energy and Administering Insulin During Follicular Growth," *J. Anim. Sci.,* 1987, 507–516, vol. 64.
Gill, J.L., et al., "Analysis of Repeated Measurements of Animals," *J. Anim. Sci.,* 1971, 331–336, vol. 33.
Harmon, D.L., "Impact of Nutrition on Pancreatic Exocrine and Endocrine Secretion in Ruminants: A Review," *J. Anim. Sci.,* 1992, 1290–1301, vol. 70.
Harrison, L.M., et al., "Influence of Insulin and Energy Intake on Ovulation Rate, Luteinizing Hormone and Progesterone in Beef Heifers," *J. Anim. Sci.,* 1986, 1228–1235, vol. 63.
Hart, I.C., "Endocrine Control of Nutrient Partition in Lactating Ruminants," *Proc. Nutr. Soc.,* 1983, 181–194, vol. 42.
Hoefler, W.C., et al., "Influence of Suckling Status and Type of Birth on Serum Hormone Profiles and Return to Estrus in Early–Postpartum Spring–Lambing Ewes," *Theriogenology,* Jun. 1987, 887–895, vol. 27, No. 6.
Hunter, R.A., et al., "The Effect of Supplements of Formaldehyde–Treated Casein on the Partitioning of Nutrients between Cow and Calf in *Lactating Bos Indicus x Bos taurus* Heifers Fed a Roughage Diet," *Aust. J. Agric. Res.,* 1988, 1151–62, vol. 39.
Lalman, D., et al., "The Effects of Ruminally Undegradable Protein, Propionic Acid and Monensin on Puberty and Reproductive Efficiency in Beef Heifers," *Proceedings, Western Section, American Society of Animal Science,* 1991, vol. 42.
Merriam, G.R., et al., "Algorithms for the Study of Episodic Hormone Secretion," *Amer. J. Physiol.,* 1982, E310, vol. 243.
Petersen, M.K., et al., "The Metabolic Effects of Supplementing Mature Blue Grama Hay with Different Sources of Protein to Yearling Ewes," *Cattlemen,* Mar. 1992, 61–62.
Pope, T.C., et al., "Effect of Insulin on the Concentration of Glucose and Hormones in Serum and Milk Yield of Postpartum Ewes," *Can. J. Anim. Sci.,* 1991, 1257–1260, vol. 71.
Sanson, D.W., et al., "Growth Response, Carcass Characteristics and Serum Glucose and Insulin in Lambs Fed Tolazamide," *Nutr. Rep. Int.,* Feb. 1984, 461–471, vol. 29, No. 2.
Wiley, J.S., et al., "Production from First–Calf Beef Heifers Fed a Maintenance or Low Level of Prepartum Nutrition and Ruminally Undegradable or Degradable Protein Postpartum," *J. Anim. Sci.,* 1991, 4279, vol. 69.

*Primary Examiner*—Chhaya D. Sayala
*Attorney, Agent, or Firm*—Rod D. Baker; Deborah A. Peacock; Brian J. Pangrle

[57] ABSTRACT

Disclosed are methods of altering blood constituents in grazing animals. Serum concentrations of serum insulin, serum urea nitrogen, serum glucose, and serum growth hormone in ruminants were varied by feeding specific protein supplements and an otherwise negative energy diet. Protein supplements were selected both from high rumen-degradable proteins, such as cottonseed meal, and low rumen-degradable proteins, such as blood and feather meals. Improvement in body condition and body weight was concomitant with reduced milk production.

18 Claims, 8 Drawing Sheets

METHOD OF IMPROVING EFFICIENCY IN RUMINANTS

CROSS-REFERENCE TO RELATED APPLICATIONS

This application is a divisional of application Ser. No. 08/516,252 filed on Aug. 17, 1995, now U.S. Pat. No. 5,672,366 which is a file-wrapper-continuation of Ser. No. 08/087,493 filed on Jul. 6, 1993, abandoned.

BACKGROUND OF THE INVENTION

1. Field of the Invention (Technical Field)

The invention relates to animals and more particularly to a process of increasing efficiency in ruminant animals.

2. Background Art

Previous studies have suggested that protein nutrition may stimulate insulin release (Hunter, R. A., et al., "The Effects of Formaldehyde-Treated Casein on the Partitioning of Nutrients between Cow and Calf in Lactating Bos Indicus x Bos Taurus Heifers Fed a Roughage Diet", Aust. J. Agric. Res. 39:1151, 1988); Laiman, et al., "The Effects of Ruminally Undegradable Protein, Propomic Acid and Monecim on Puberty and Reproduction Efficiency in Beef Heifers", Proc. West. Sec. Amer. Soc. Anim. Sci. 42, 1991; Wiley, et al., "Production from First Calf Beef Heifers Fed a High or Low Level of Prepartum Nutrition and Ruminally Undegradable or Degradable Protein Postpartum." J. Anim. Sci. 69:4279, 1991.

A study conducted by Applicant and others (Petersen, et al., "The Metabolic Effects of Supplementing Mature Blue Grama Hay with Different Sources of Protein to Yearling Ewes," published March, 1992), revealed that serum insulation concentration increased with protein supplementation. It was further concluded that feather meal protein supplement resulted in the highest concentration of serum insulin concentration compared with ewes consuming either cottonseed meal or blood meal protein supplement. Ewes receiving the cottonseed meal protein supplement, however, had the highest serum glucose concentrations; generally nonsupplemented control ewes had lower serum glucose concentrations than supplemented ewes.

Further, nonsupplemented ewes had lower blood urea nitrogen concentrations than supplemented ewes.

None of the prior art developed to date, however, has taught or suggested that different protein sources may elicit differential responses in insulin release, serum glucose concentration, serum growth hormone concentration. Further, none of the prior art has disclosed or suggested that re-partitioning of nutrients in ruminants may be differentially affected by ingestion of various protein sources.

SUMMARY OF THE INVENTION (DISCLOSURE OF THE INVENTION)

In accordance with the present invention there is provided a method for altering grazing animals blood constituents. The method comprises the steps of: selecting a protein dietary supplement affecting the serum concentration of at least one blood constituent selected from the group consisting of serum insulin, serum urea nitrogen, serum glucose and serum growth hormone; administering the protein dietary supplement; and providing additional protein in the daily feed allotment while otherwise maintaining a negative energy diet.

The method further comprises the step of selecting a protein dietary supplement having a high rumen-degradable protein, or selecting a protein dietary supplement having a low rumen-degradable supplement. The step of selecting a protein dietary supplement comprises the step of selecting a supplement from the group consisting of feather meal, cottonseed meal, blood meal and mixtures thereof. The method further comprises the step of selecting feather meal, or cottonseed meal, or blood meal. The method further comprises the step of selecting a mixture of blood meal and cottonseed meal, or feather meal and cottonseed meal, or blood meal and feather meal, or a mixture of cottonseed meal, feather meal and blood meal.

The method further comprises the steps of selecting specific animal efficiency parameters in ruminants from the group consisting of body condition, body weight, milk production, reproduction and offspring weight; and administering said protein dietary supplement chosen to augment at least one of the selected specific animal efficiency parameters. The step of selecting specific animal efficiency parameters comprises the step of selecting reproduction and offspring weight. The step of administering selected supplements further comprises the step of withholding protein supplements. Selecting specific animal efficiency parameters comprises the step of selecting decreased milk production.

An object of the invention is the provision of a method providing release of serum insulin, serum urea nitrogen; serum glucose and serum growth hormone in ruminants by selected dietary supplements.

Yet another object of the invention is the provision of a method providing increase of body condition and body weight in ruminants receiving a negative energy diet.

Still another object of the invention is the provision of a decrease in milk production; with a concomitant increase in body condition and body weight.

An advantage of the invention is the simple augmentation of selected animal efficiency parameters by proper selection of dietary supplements.

Another advantage of the invention is its relative low cost relative to results achievable.

Yet another advantage of the invention is its relative practicality.

Still another advantage of the invention is the use of dietary protein supplements having little other food value.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

Figure 1:
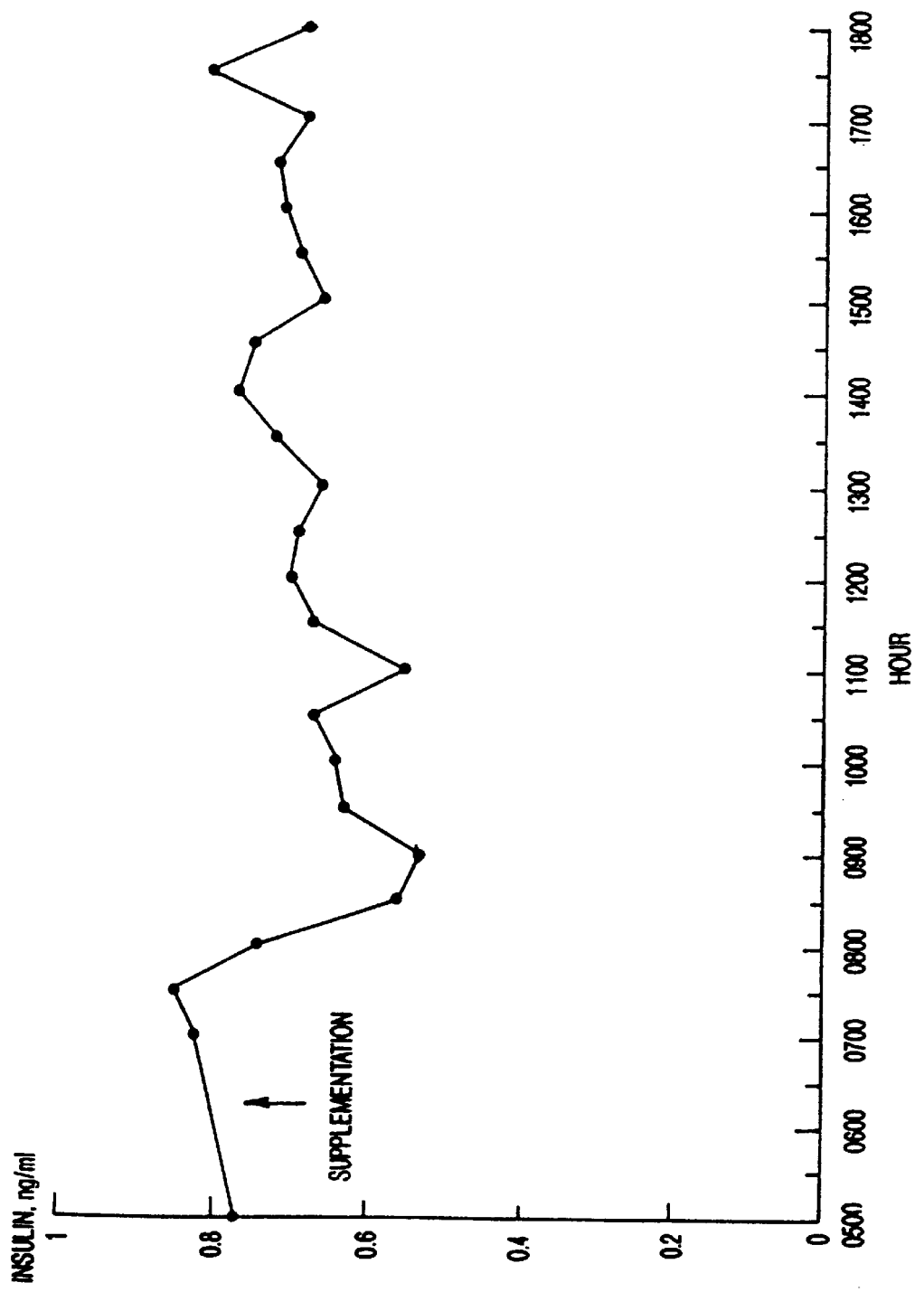
FIG. 1 is a curve showing the effect of time on serum insulin concentration.

DESCRIPTION OF THE PREFERRED EMBODIMENTS (BEST MODES FOR CARRYING OUT THE INVENTION)

The invention comprises the re-partitioning of nutrients in ruminant animals. Specifically, ruminants normally fed a decreased energy diet are additionally fed a protein supplement. The protein supplement may comprise a variety of protein sources, including feather meal, blood meal, cottonseed meal and various combinations of these sources.

Generally, test results showed that increased serum insulin, the result of protein supplementation, ultimately resulted in improved body condition and body weight at the end of the test period. Concomitantly, milk production was decreased.

Further, growth hormone is reduced in protein supplemented ruminants, while serum glucose is increased by protein supplementation. Blood urea nitrogen is also increased in ruminants fed supplemental protein.

Industrial Applicability

The invention is further illustrated by the following non-limiting examples. In each of the examples, a negative energy diet is provided to all subject animals.

EXAMPLE 1

Twenty eight Debouillet ewe lambs [average body weight (BW) 45.7 kilograms (kg)] were individually housed indoors and fed blue grama hay at a rate of 1.5% of body weight for 17 days. Water was available at all times. The rate of feeding was used to minimize differences in feed intake. The hay contained 8.1% crude protein (CP) and was chopped to approximately 2.5 cm through a grinder mixer. The daily hay was fed at 1800 hours along with 180 grams of sun-cured alfalfa pellets. Alfalfa pellets were added to ensure adequate ruminal nitrogen availability for microbial digestion of the hay. Each day each ewe was fed one of nine supplement combinations. The first group (n=4) served as a negative control (CON) and received no additional nutrients at 0700 hours. An energy control was formulated with corn (C) and no supplemental protein. This supplement was used to compare with supplements supplying similar quantities of energy (112 grams total digestible nutrients (TDN) per day) but total digestible nutrients greater amounts of crude protein (CP). The first protein supplement, used cottonseed meal (CSM) as a protein source and supplied 97.8 grams of crude protein/day (CP/d). This supplement contained the greatest amount of ruminally degradable protein and total digestible nutrients (TDN) (150 grams/day). It was also considered as a positive control. The remaining seven supplements were formulated with blood meal (BM) and/or feather meal (FM) and combinations of corn or cottonseed meal. These were formulated to be isoenergetic with corn and isonitrogenous with cottonseed meal. Because blood meal and feather meal protein are less ruminally degradable than cottonseed meal (NRC, 1985), the quantity of ruminally undegradable protein varied. Supplements utilizing blood meal or feather meal as the sole protein source were mixed with corn to increase the total digestible nutrient content. The remaining three supplements contained 50% of the protein from cottonseed meal and the other 50% from either blood meal (cottonseed meal plus blood meal) or feather meal (cottonseed meal plus feather meal) or blood meal and feather meal (cottonseed meal plus blood meal plus feather meal), as shown in Table 1.

TABLE 1

FORMULATION OF SUPPLEMENTS USING CORN (C), COTTONSEED MEAL (CSM), BLOOD MEAL (BM) OR FEATHER MEAL (FM) ON DRY MATTER BASIS

|  | C | CSM | C + BM | C + FM | BM + FM | CSM + BM | CSM + FM | CSM + FM + BM |
|---|---|---|---|---|---|---|---|---|
| Ingredient (%) | | | | | | | | |
| Corn | 89.5 | | | | | 27.8 | 28.6 | 28.2 |
| CSM | | 100 | | | | 61.2 | 62.7 | 61.9 |
| BM | | | 63.7 | | 32.5 | 34.3 | | 17.3 |
| FM | | | | 64.3 | 31.5 | | 33.6 | 16.6 |
| Dicalcium Phosphate | 7.2 | | 5.5 | 4.2 | 4.8 | 2.9 | 2.1 | 2.5 |
| Potassium chloride | 3.3 | | 3.0 | 2.9 | 2.8 | 1.6 | 1.5 | 1.6 |
| Estimated composition (g/d) | | | | | | | | |
| DM | 140 | 200 | 167 | 159 | 163 | 163 | 159 | 161 |
| CP | 12.6 | 97.8 | 97.8 | 97.8 | 97.8 | 97.8 | 97.8 | 97.8 |
| Undegradable CP | 6.3 | 42 | 78.7 | 68.5 | 73.5 | 61.1 | 55.7 | 58.4 |
| Total Digestible nutrients | 112 | 150 | 112 | 112 | 112 | 112 | 112 | 112 |
| Phosphorus | 2.0 | 2.0 | 2.0 | 2.0 | 2.0 | 2.0 | 2.0 | 2.0 |
| Potassium | 2.8 | 2.8 | 2.8 | 2.8 | 2.8 | 2.8 | 2.8 | 2.8 |

During a 16 day adaption period, four ewes did not consume their entire daily supplement at the morning feeding and were allowed access to it throughout the day. Ewes that had a history of supplement refusals received their refused feed by gavage on day 17 of the study within 30 minutes of feeding.

At early morning, 60 minutes before supplement feeding on day 17, 10 ml blood samples were collected via jugular puncture and centrifuged at 2,000 rpm for 30 minutes. The serum was immediately decanted and frozen for future analysis. After morning supplement consumption, blood samples were collected every 30 minutes for 11 hours and prepared as described above. Samples collected every 30 minutes were analyzed for insulin by RIA (Sanson and Hallford, 1984). Samples collected every hour were analyzed for growth hormone (G.H.) (Hoefier and Hallford, 1987), glucose and urea nitrogen.

The serum insulin, growth hormone (GH), glucose and urea were analyzed by split plot analysis of variance for repeated measures. Effects of supplementation was tested using ewe (treatment) as the error term while time of sampling was tested using the residual as the error term. If an hour by supplement interaction was detected, supplement effects were analyzed within an hour. Means were compared using the following preplanned linear contrasts: control versus others, corn versus protein, cottonseed meal versus blood meal and feather meal, cottonseed meal versus no cottonseed meal, blood meal versus feather meal, blood meal and feather meal versus cottonseed meal plus blood meal and cottonseed meal plus feather meal and cottonseed meal plus blood meal plus feather meal versus protein.

TABLE 2

Mean 12 hour Serum Insulin Concentration in Ewes fed Various Protein Supplements

| Protein Source[a] | Insulin ng/ml[b][c] |
|---|---|
| None | 0.25 |
| Corn | 0.65 |
| CSM | 0.85 |
| BM + CSM | 1.0 |
| BM | 0.71 |
| FM + CSM | 0.6 |
| FM | 1.2 |
| FM + BM | 0.68 |
| FM + BM + CSM | 0.31 |

[a]CSM = cottonseed meal, BM = blood meal, FM = feather meal
[b]Control standard error = .065; all other standard error = .035.
[c]None vs. other (P < .06), BM vs. FM (P < .02), BM + FM + CSM vs. supp (P < .01).

Figure 2:
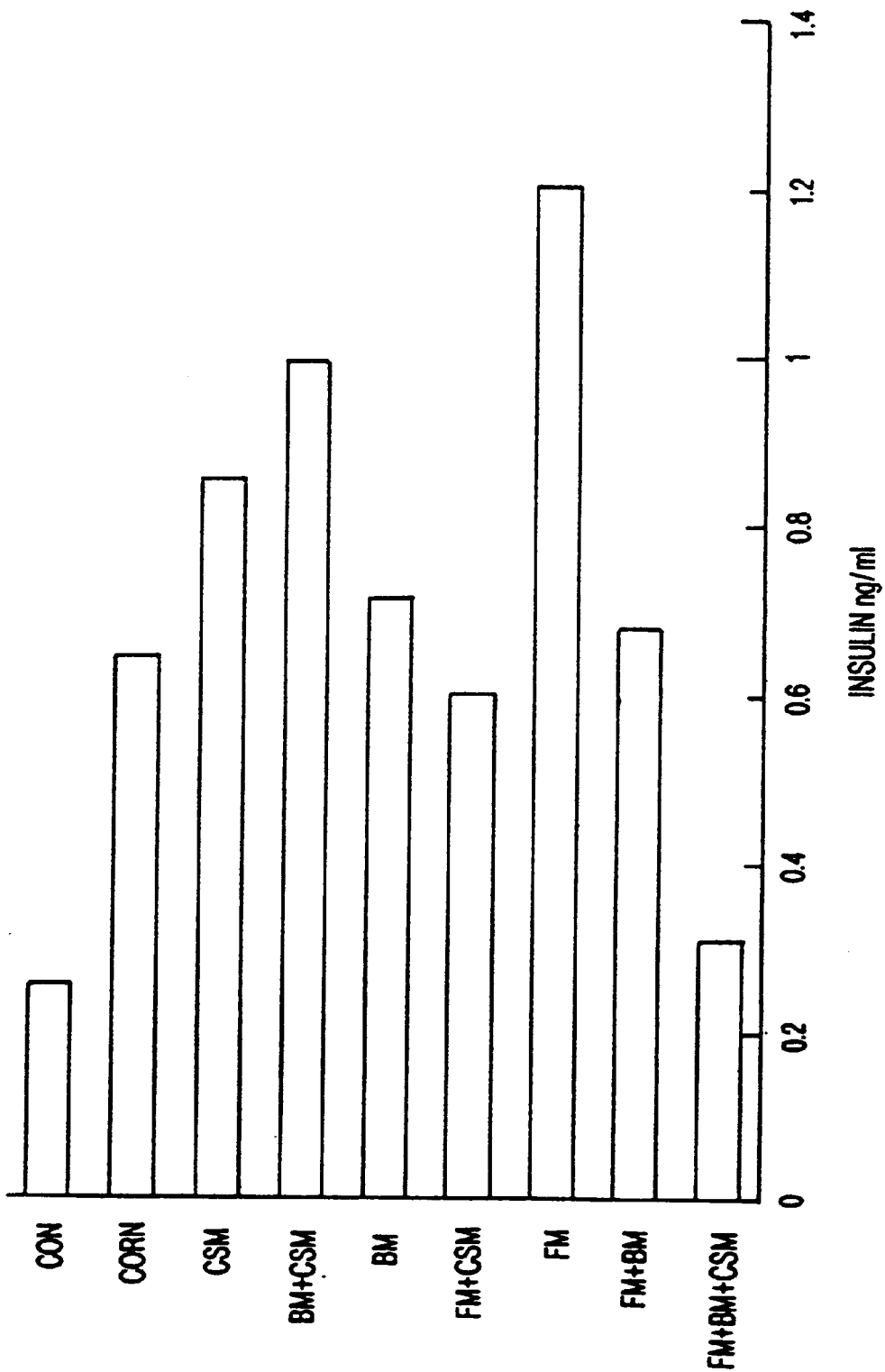
FIG. 2 is a bar graph showing serum insulin in ewes fed various protein sources, corn and control.

Supplement and sampling time after feeding did not interact to affect serum insulin concentration. Sampling hour influenced (Probability<0.01) insulin concentration. The greatest concentration was found 90 minutes and the lowest concentration occurred 240 minutes after supplement intake as shown in FIG. 1. Supplementation altered (probability<0.01) serum insulin concentrations as shown in FIG. 2. Ewes that were fed supplement had higher (probability=0.05) insulin concentrations than ewes that were assigned to the control treatment. Corn supplemented ewes had similar insulin concentrations as protein supplemented ewes. As shown in Table 2, feather meal fed ewes had the highest concentration (1.2 ng/ml) which was greater (probability<0.01) than the blood meal fed ewes. Ewes fed the combination of blood meal plus feather meal plus cottonseed meal had concentrations that were lower than any other protein supplement group. Ewes fed the combination of cottonseed meal with blood meal or feather meal had similar insulin concentration as those fed blood meal or feather meal alone. The quantity of protein fed did not vary, so the variation in serum insulin is due to protein source. It appears that the quantity of ruminally undegradable intake protein has little influence on serum insulin concentration because the feather meal and blood meal groups received the greatest quantity of undegradable intake protein (UIP) but these two supplements elicited different responses. Ewes fed the cottonseed meal supplement received the smallest quantity of undegradable intake protein but did not have the lowest values. The group that had the lowest value received the three-way combination which would be expected to have the highest biological value due to the complementary nature of these protein sources. In contrast, ewes fed the supplement with the lowest biological value, feather meal, had the highest insulin concentration. This relationship is interesting in that the supplement with the highest biological value had the lowest insulin concentration and the supplement with the lowest biological value had the highest insulin concentration. Harmon (1992) reported that dietary protein is a potent stimulator of insulin release in comparison to glucose and propionate. It is possible that the concentration of specific amino acids partially regulate insulin release.

Figure 3:
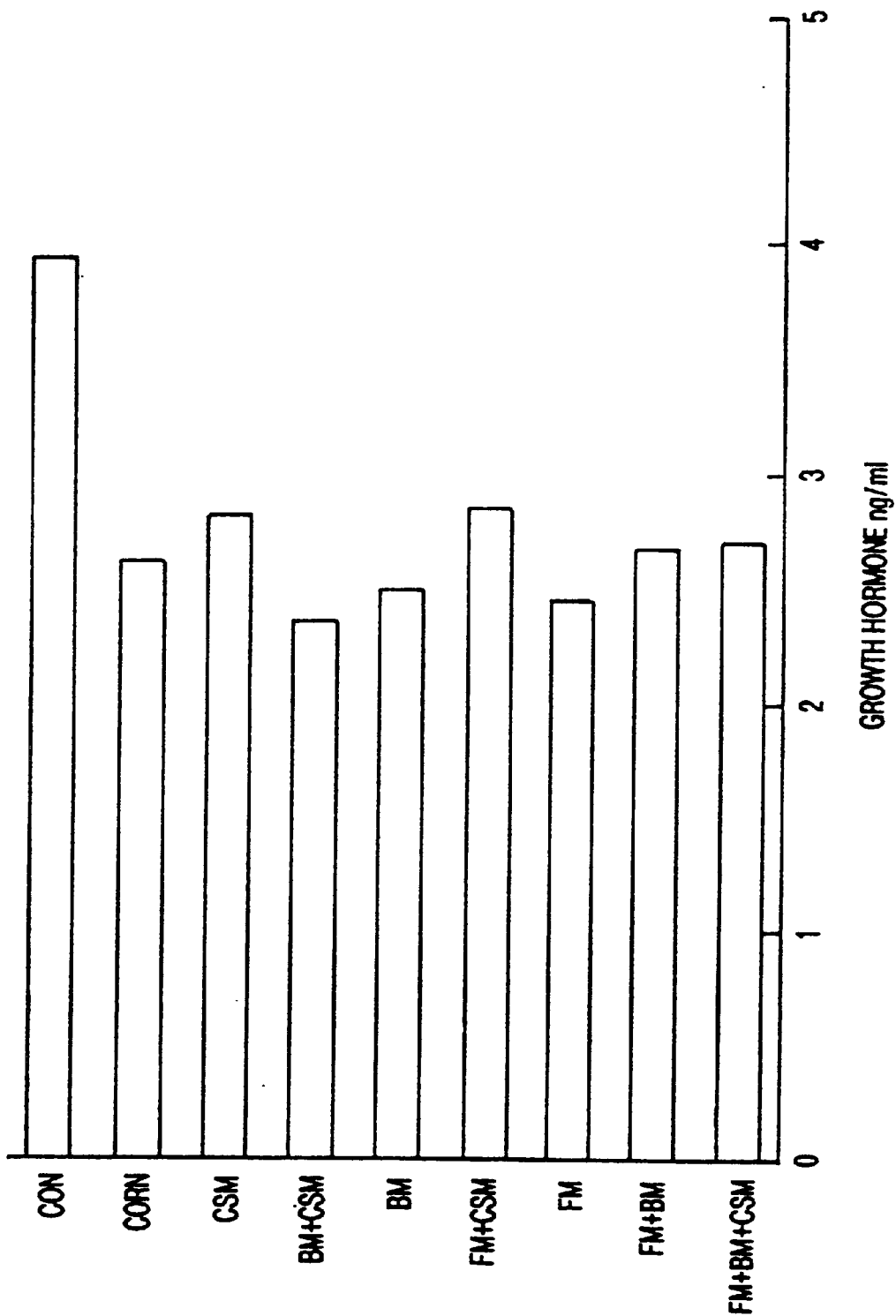
FIG. 3 is a bar graph showing serum growth hormone in ewes fed differing quantities and protein sources.
Figure 4:
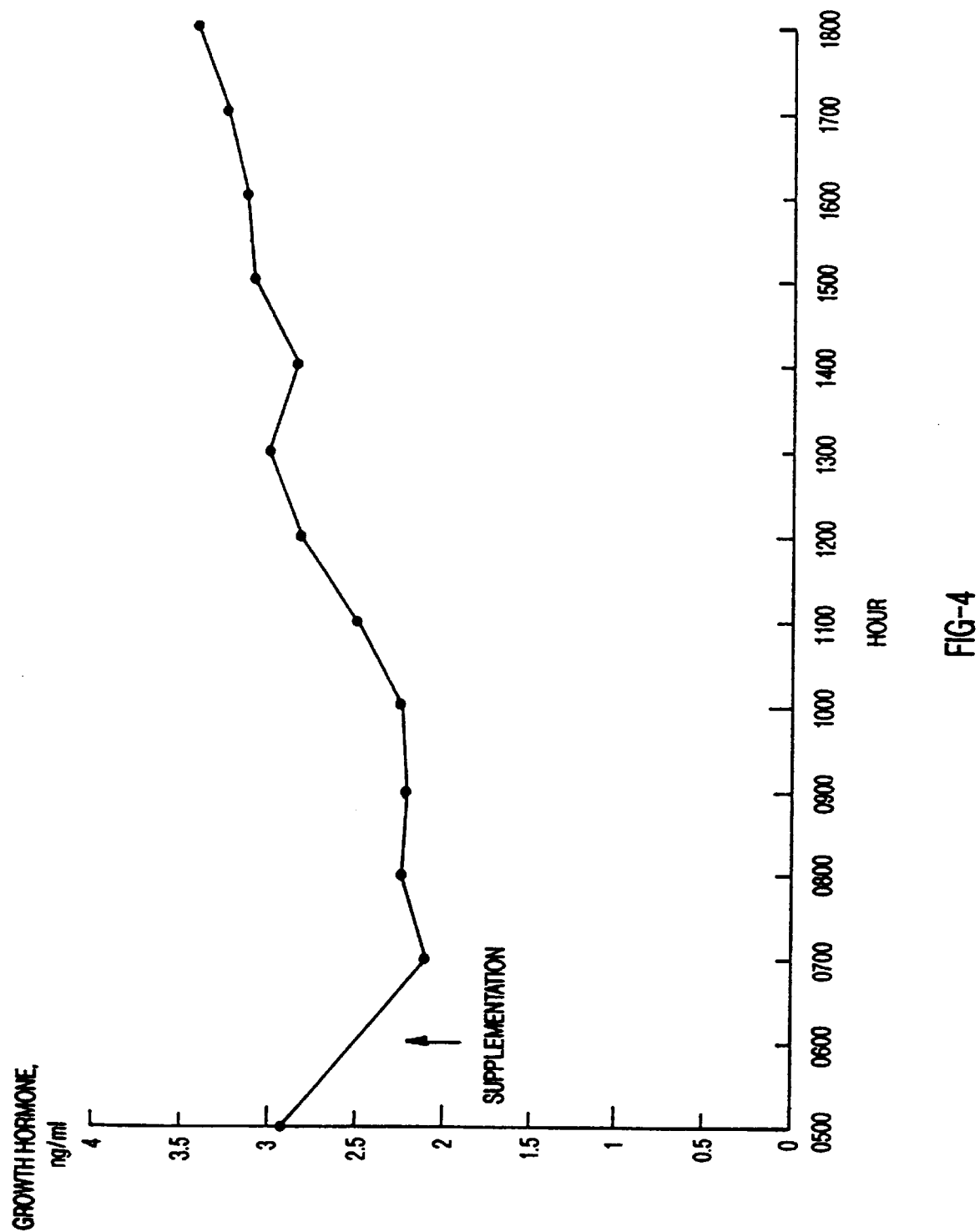
FIG. 4 is a curve illustrating the effect of time on serum growth hormone.
Figure 5:
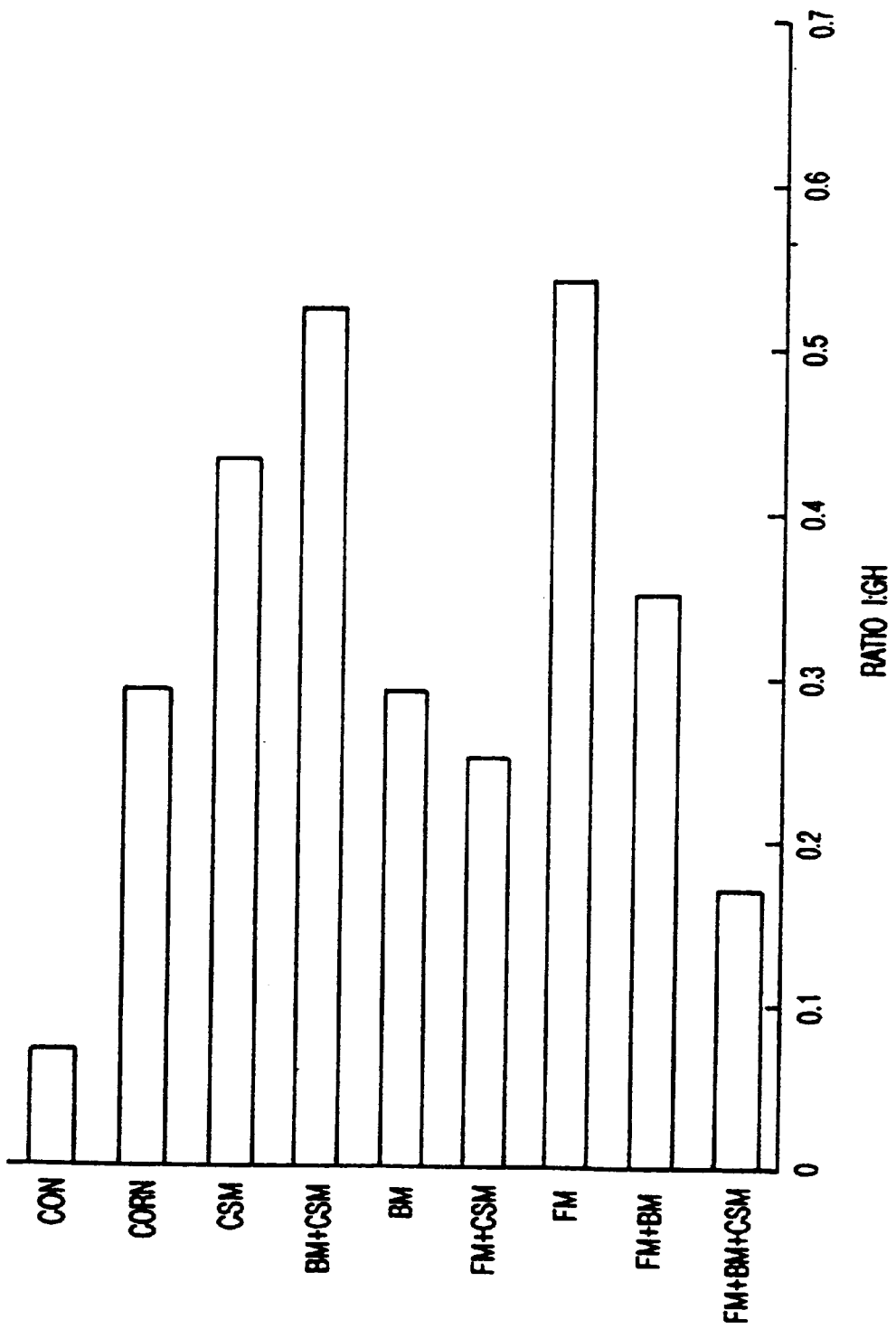
FIG. 5 is a bar graph showing the ratio of serum insulin to growth hormone concentration.

Growth hormone concentration was greatest (probability<0.01) in the control fed ewes with all other groups having similar concentrations as shown in FIG. 3. Sampling time influenced growth hormone concentration. Arter supplementation the concentration of growth hormone increased as shown in FIG. 4. The ratio of insulin to growth hormone was influenced to the greatest extent by insulin concentration, except in the control fed ewes that had elevated growth hormone concentrations. Ewes fed feather meal had a higher (probability<0.05) ratio than the blood meal fed ewes while ewes receiving the combination supplement cottonseed meal plus blood meal plus feather meal had a lower ratio than the supplemented groups. Time after supplementation influenced (probability<0.01) the ratio of insulin to growth hormone. The ratio declined after feeding as shown in FIG. 5. Sampling time and supplement did not interact to influence growth hormone or the insulin: growth hormone ratio.

Figure 6:
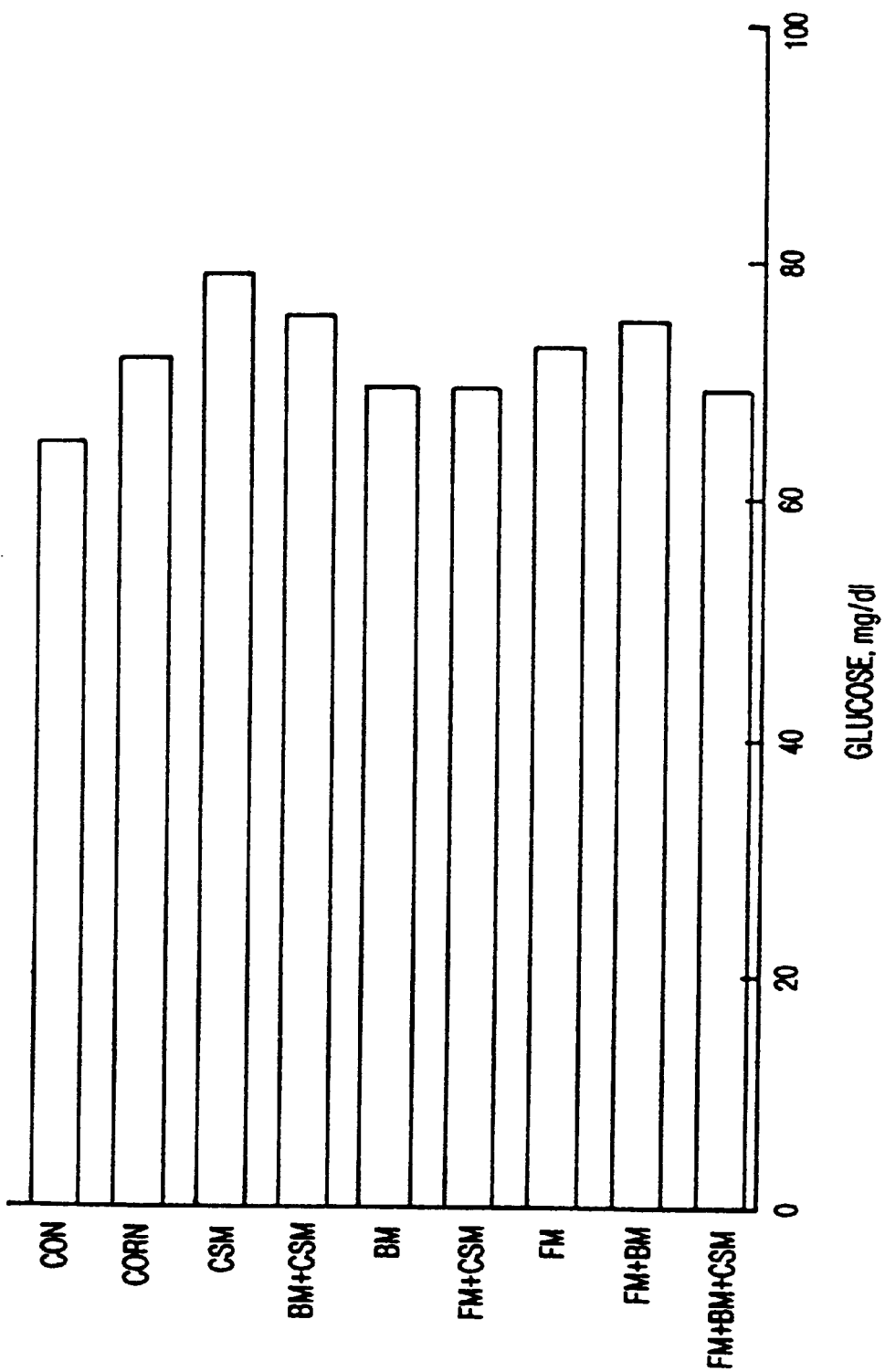
FIG. 6 is a bar graph showing serum glucose in ewes fed different protein sources.
Figure 7:
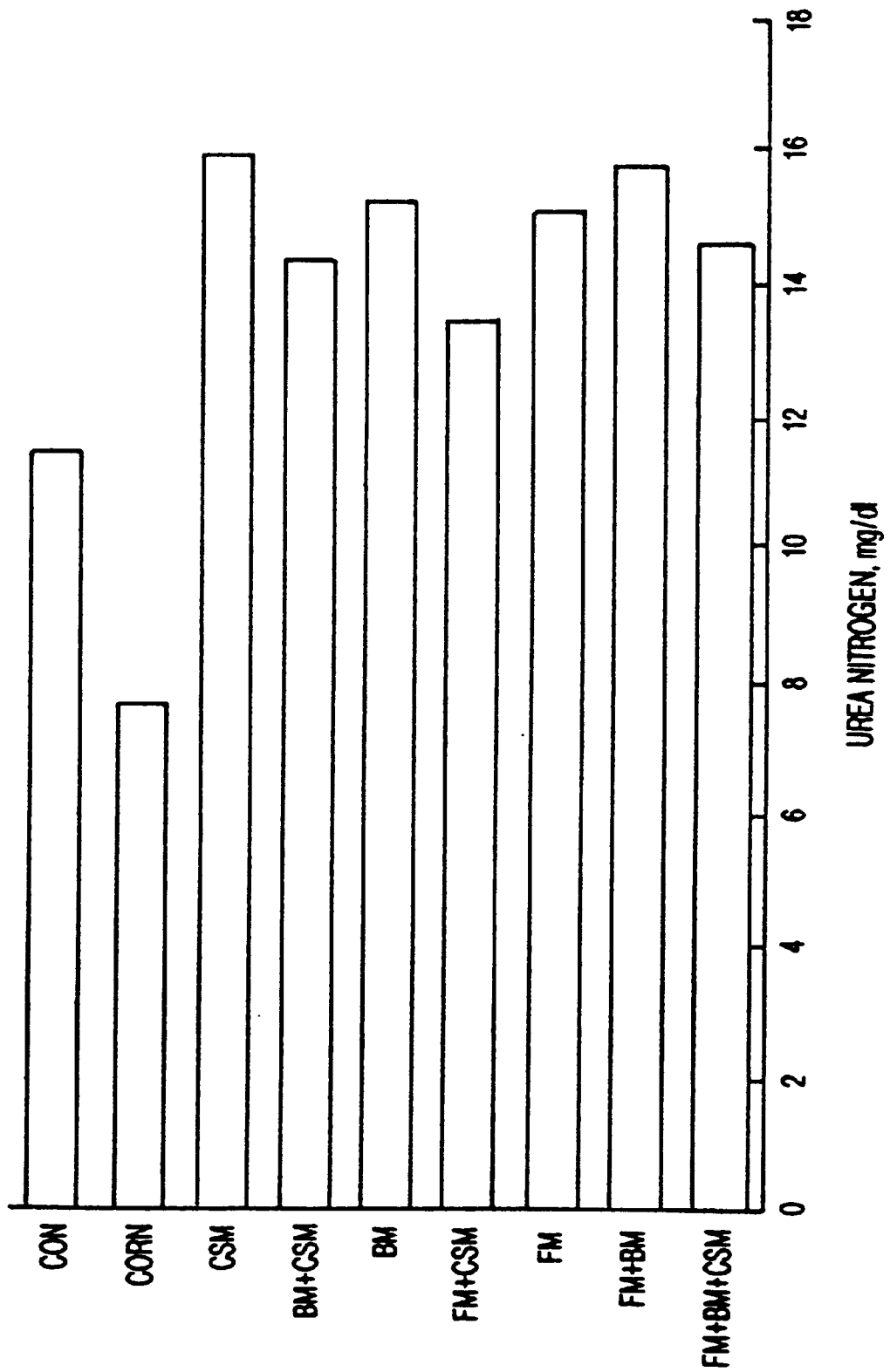
FIG. 7 is a bar graph showing blood urea nitrogen in ewes fed differing quantities and sources of protein.

Serum glucose concentration was also influenced (probability<0.01) by supplementation. Ewes consuming the control treatment had the lowest (probability<0.01) glucose concentrations while ewes fed cottonseed meal plus blood meal plus feather meal had the lowest (probability<0.05) concentration of the supplemented ewes. Ewes fed cottonseed meal had greater (probability<0.01) serum glucose than the blood meal and feather meal supplemented ewes (FIG. 6). Serum urea nitrogen was also influenced by supplementation. Serum urea nitrogen is a measurement that is indicative of the metabolic distribution of dietary protein. It is not a "key" regulatory metabolite with capabilities comparable to insulin, growth hormone or glucose. Ewes receiving control had lower (probability<0.10) serum urea nitrogen than those fed supplement. However, ewes fed corn had at least a 50% lower serum urea nitrogen concentration (probability<0.01) than supplemented ewes and 25% lower serum urea nitrogen content than control ewes (FIG. 7). Ewes receiving the protein supplements were fed approximately 75% above NRC (1985) requirements while the control-treated ewes were fed approximately 35% and corn fed ewes 30% below the NRC (1985) requirement for 50 kilogram ewe lambs gaining 100 grams a day. It is expected that the control-treated ewes should have a serum urea nitrogen value less than the protein supplemented ewes; however, corn-fed ewes were the lowest. The supplemental corn probably stimulated ruminal microbial growth and increased the utilization of ruminal nitrogen and therefore caused a decline in serum urea nitrogen and probably an increase in the flow of microbial protein available for absorption. The corn treatment was designed to serve as an energy control, which it did, but is probably also confounded by microbial protein synthesis. As indicated by the depressed serum urea nitrogen, microbial protein flow may have increased and therefore offset comparisons of increases to feed protein flowing to the small intestine with a high energy low protein supplement. The effects of protein and energy intake cannot be completely separated in this study.

The objective of this study example was to determine if different sources of protein would elicit differential responses in insulin release. Ewes fed feather meal had the highest serum insulin concentration, while those fed the cottonseed meal plus blood meal plus feather meal combination had the lowest. The difference between these ewes was nearly fourfold. Therefore, sources of protein have divergent effects. There was a trend for ewes with the highest insulin concentration to also have lower glucose concentration (cottonseed meal versus feather meal fed ewes) which may be indicative of a dietary means for nutrient partitioning.

Effects on growth, milk production, intake and birth weight have been reported due to different sources of protein. These results generally have been attributed to biological value of the protein sources evaluated. However, it is submitted that some of these responses resulted from changes in metabolic hormone status rather than satisfying a nutrient limitation.

EXAMPLE 2

Thirty two primiparous Angus x Hereford range beef cows with an average initial body weight of 359.1±5.7 kg were used in a completely random design to investigate effects of exogenous insulin on postpartum reproduction. After calving, cows in thin body condition (4.5±0.08) were delivered to the NMSU Livestock Research Center, Las Cruces, N. Mex. from the NMSU Corona Range Livestock Research Center, Corona, N. Mex. and were randomly assigned to one of eight pens (four cows/pen) followed by treatment assignment to pens (four pens/treatment). Sire-of-calf (Longhorn or Red Angus) was stratified across pens.

Treatments consisted of daily subcutaneous injections of either 50 IU Lente insulin$^2$ animal$^{-1}$.d$^{-1}$ (INS) or 0.5 mL physiological saline.animal$^{-1}$.d$^{-1}$ control (CON). Treatments were initiated approximately 3 weeks postpartum and continued for 39 days. Initially, insulin dosage was 150 IU.animal$^{-1}$.d$^{-1}$ similar to that which was administered to postpartum ewes on a body weight basis (Pope and Hallford, 1991); however, some insulin-treated cows began to experience signs of insulin shock (hypoglycemia) 4 days after treatments began. One cow was removed from the study due to blindness caused by insulin shock. Treatments were discontinued on day 5 and day 6 of the treatment period and resumed on day 7 with a reduced dosage (50 IU.animal$^{-1}$.d$^{-1}$) throughout the remainder of the 39th day period with the exception of three cows. These three cows received 33 IU.animal$^{-1}$.d$^{-1}$ because they continued to display signs of hypoglycemia in the late afternoons at the higher dosage. Furthermore, these cows were lower in body eight and were in very thin body condition (<4).

TABLE 3

Nutrient analysis of forages fed to primiparous beef cows after calving (DM basis)

| Forage | DM, % | CP, % | NDF, % |
|---|---|---|---|
| Prairie Hay | 93.2 | 5.4 | 67.3 |
| Alfalfa | 93.5 | 19.0 | 34.8 |

Cows were pen fed a grass hay-alfalfa diet (80%–20%) at approximately 2.5% of their body weight (83 and 94% of crude protein and total digestible nutrient requirements, respectively, NRC, 1984) during the treatment period. Pen size was 12×15 m with S m of bunk space provided to allow cows free access to feed at all times. Cows also were provided free access to a salt and mineral (Ca and P) supplement during the drylot period. After the insulin treatment period cows were combined in a common drylot breeding pen. Cows were fed a grass hay-alfalfa ration (50%–50%), at 2.5% of body weight through the first 21 days of breeding. In the second 21-day period of breeding, the ratio of grass hay to alfalfa was decreased (25%:75%), and the percentage of body weight fed was increased (2.75%). During the last period of drylot conditions, cows were fed 100% alfalfa at 2.75% of body weight. Feeding management was devised to reflect increasing nutrient quality and quantity of grazed forage found in native spring range. Nutrient analysis is shown in Table 3. Cows were exposed to one of two fertile Angus bulls (alternating weekly) equipped with a chin-ball marker during drylot breeding. They were returned to the NMSU Corona Range Livestock Research Center where they were managed as a group for the remainder of the breeding season and until calves were weaned. Cow weights were recorded at the same hour (1000 hours to 1100 hours) of each day at the beginning of the study and at approximately 21 day intervals during drylot breeding. Calf weights were measured at birth, end of the drylot period, and at weaning. Cow condition scores were evaluated by three technicians (1=emaciated, 9=obese) prior to the study, after the treatment period, and upon completion of drylot breeding.

Ten milliliters of blood were collected from cows via jugular venipuncture at 3 day intervals during the treatment period, were centrifuged at 2300×grams for 15 minutes at 4° C. within 1 hour after collection, and serum was frozen until later analysis for progesterone (intraassay CV=4.9%) by solid phase RIA (Coat-A-Count Progesterone; Diagnostic Products, Los Angeles, Calif. First estrus postpartum was determined by chin-ball marker equipped balls during the drylot breeding period and by serum progesterone levels greater than 1 ng/mL. Furthermore, blood samples were collected and progesterone quantified by the previously described methods to confirm estrus activity before cows were returned to grazing native range. Blood was collected at 15 minute intervals over a 6 hour period that began approximately 2 hours postfeeding for determination of luteinizing hormone concentration in eight cows randomly selected from each treatment (n=16). Samples were analyzed for serum Luteinizing hormone concentration using RIA (intrassay CV=3.3%) as described by Hoefler and Hallford (1987). Luteinizing hormone (LH) pulsality was characterized for frequency, baseline, amplitude, and pulses/6 hours by analysis with Pc-Pulsar computer software (Merriam and Wachter 1982). Area under the curve was calculated for luteinizing hormone using a trapezoidal summation procedure. Fall pregnancy was determined by rectal palpation.

Blood samples were collected hourly (0600 to 1800), as previously described, for analysis of serum insulin (Sanson and Hallford, 1984), growth hormone (GH; Hoefler and Hallford, 1987), and glucose (Stanbio Colorimetric Glucose Test; San Antonio,Tex.) concentrations. lntraassay CV for insulin and growth hormone were 9.8% and 5.8%, respectively.

Milk production was estimated by using a 5 hour modified weight-suckle-weigh technique (Wiley, et al., 1991). Milk was weighed and a subsample was collected for determination of fat, lactose, protein, and solids-not-fat (Arizona Dairy Herd Improvement Association Laboratory, Phoenix, Ariz).

The main effects of treatments were analyzed using GLM procedures of SAS (1989) with means separated by appropriate t-test for the following dependent variables: cow weight and body condition score, calf weight, milk production, milk constituents and luteinizing hormone pulsatile measures. Circulating insulin, growth hormone, glucose, and luteinizing hormone concentrations were measured by split-plot ANOVA For repeated measures (Gill and Hafs, 1971). Cow within treatment was used as the testing term for treatment effects, and residual error was used to test for sample time and treatment x sample time interactions. Chi-square analysis (SAS, 1989) was used to test treatment effects for the number of cows cycling prior to their return to grazing native range and fall pregnancy rate.

Figure 8:
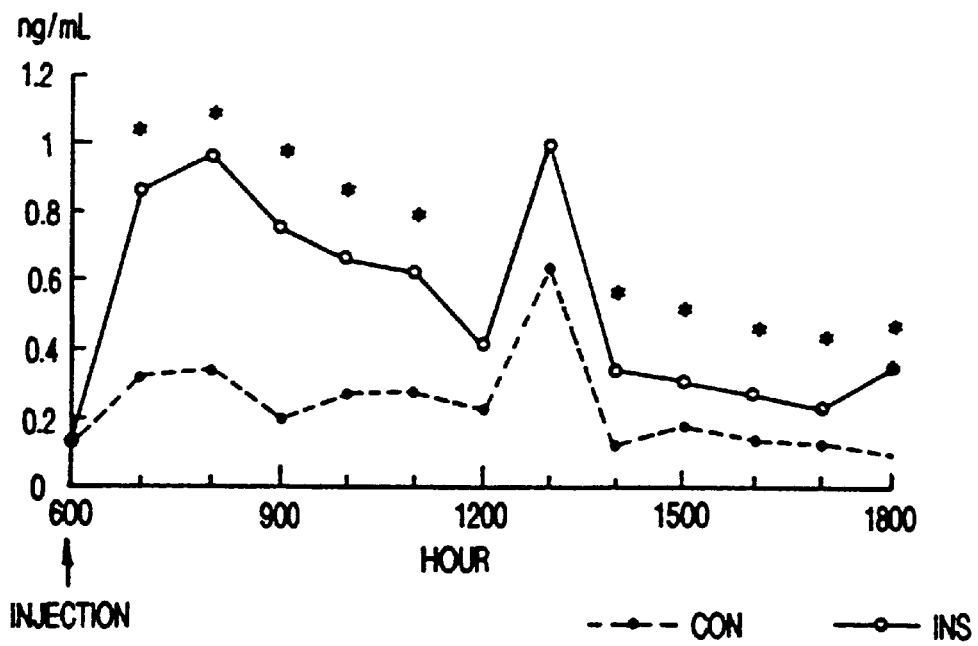
FIG. 8 is a curve showing insulin concentrations in primiparous beef cows receiving injected insulin or saline.
Figure 9:
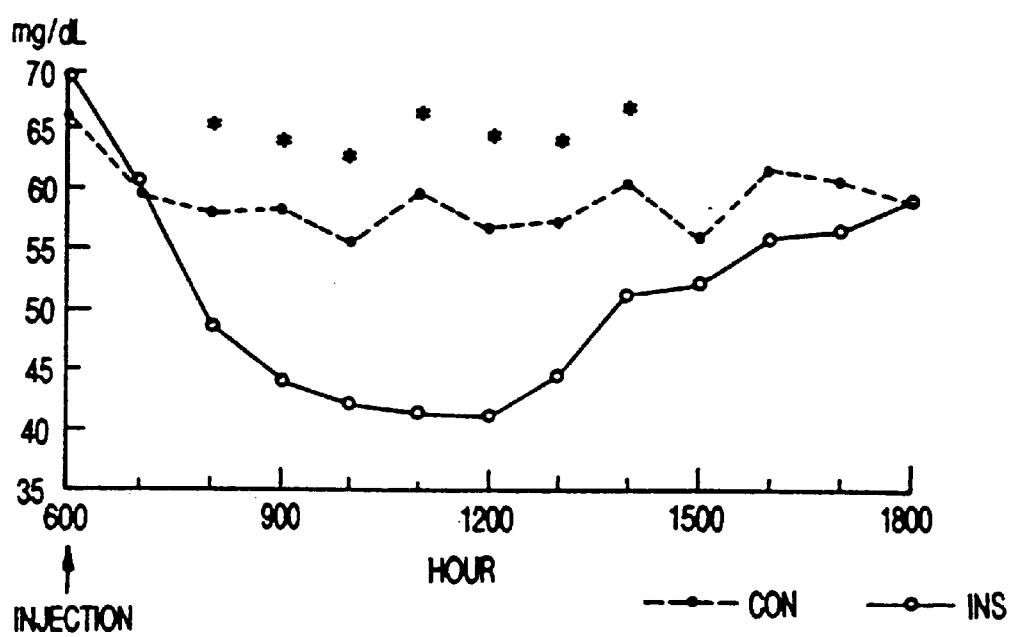
FIG. 9 is a curve showing glucose concentrations in primiparous beef cows receiving either insulin or saline injections.

It was necessary to reduce the initial insulin dosage 4 days after treatments began due to symptoms of hypoglycemia. This effect also was observed by Bellows, et al., (1964) when 320 IU of protamine-zinc insulin was administered while no symptoms occurred at 160 $IU.animal^{-1}.d^{-1}$. In sheep (Beam and Holcombe, 1992), 1 IU/kg body weight of Lente insulin was administered daily to ewe lambs without symptoms of hypoglycemia. This dosage was over two times the initial dose used in the current study (0.42 IU/kg body weight). Contradictions between Bellows, et al., (1964) or Beam and Holcombe, (1992) and the present study may have been due to the lower nutrient intake (i.e., fewer glucose precursors were available). Furthermore, cows in the present study were in their first stage of lactation during the treatment period thereby increasing glucose demand for lactose production and decreasing glucose availability to maternal tissues. Even though exogenous insulin dosage was reduced, circulating insulin and glucose concentrations were affected by treatments. Serum insulin concentrations increased (probability<0.01; as shown in FIG. 8) and glucose decreased (probability<0.05); as shown in FIG. 9) for insulin treated cows compared with control. A time x treatment interaction (probability<0.01) was detected for glucose concentration but was determined to be of little biological importance and was therefore disregarded.

TABLE 4

Milk production and milk constituents collected from primiparous cows administered s.c. injections of either saline (CON) or insulin (INS)

| | Treatment | | | |
|---|---|---|---|---|
| Item, g/d | CON | INS | SE[1] | OSL[2] |
| Milk | 4237.0 | 3201.0 | 271.5 | .01 |
| Fat | 140.5 | 118.3 | 11.5 | .18 |
| Protein | 121.0 | 108.0 | 7.4 | .22 |
| Lactose | 204.2 | 148.8 | 12.6 | .004 |
| Snf[3] | 350.5 | 276.4 | 21.3 | .02 |

[1]Standard error of least squares means, n = 15 cows.
[2]Observed significance level of least squares means.
[3]Snf = solids-not-fat Cows that received insulin lost body weight (0.9±1.8 kg) while control cows gained body weight (4.3±1.8 kg) during the treatment period (probability<0.05). However, by the end of the drylot period, insulin-treated cows had compensated, resulting in similar body weight gain over combined treatment and drylot breeding periods (17.5±3.1 kg). Body condition was less (probability<0.07) for insulin treated cows (4.4±0.08) compared to control cows (4.6±0.08) at the beginning of the study. Yet, at the end of drylot breeding, body condition (4.8±0.08) was similar (probability=0.62) between treatments. This may suggest that cows treated with insulin increased body reserves in the form of adipose tissue or changed metabolism to favor energy storage during the postpartum period more quickly than control cows. The source of energy to increase body condition, since feed intake was similar in both treatments, may have resulted from a re-partitioning of nutrients and lowered milk production (probability<0.01) in insulin-treated cows compared to control cows as shown in Table 4. Grams of lactose and solids-not-fat secreted also were reduced (probability<0.02) while grams of milk fat and protein were unaffected (probability>0.18) by treatments as shown in Table 4. A decrease in milk production agrees with Hunter and Magner (1988) who increased insulin with formaldehyde treated casein in beef cows and with data in goats treated with insulin (Chang and Young (1992); however, re-partitioning of nutrients in these studies resulted in increased body weight gain. It was hypothesized in the present study that energy conserved by lowered milk production of insulin-treated cows was partitioned towards fat synthesis while control cows had lowered lipogenesis and greater milk production in the absence of insulin. It is unclear why a body weight advantage for insulin cows did not occur during the treatment period, but was possibly due to adverse effects from the initial insulin dosage. High concentrations of growth hormone during lactation are believed to facilitate the diversion of nutrients, such as glucose and lipid, to the mammary gland to meet the nutrient demand for milk production (Hart, 1983). Growth hormone concentration, although numerically lower for insulin cows versus control treated cows (7.2 vs. 8.4±0.7 ng/mL, respectively), were not statistically different (probability= 0.24). Due to lower milk production in insulin treated cows, it would be predicted that calf growth would be depressed. However, calf weights were similar (92.9±2.8 kg, P=0.72) at the end of drylot breeding and at weaning (125.6±4.0 kg; P=0.88insulin- and control-treated cows.

TABLE 5

Luteinizing hormone (LH) pulsatility and area under the curve measurements collected from primiparous cows administered s.c. injection of either saline (CON) or insulin (INS)

| | Treatment | | | |
|---|---|---|---|---|
| Item | CON | INS | SE[1] | OSL[2] |
| Mean, ng/mL | 1.04 | .96 | .12 | .63 |
| Frequency, ng/mL | .017 | .017 | .002 | .99 |
| Baseline, ng/mL | .78 | .65 | .10 | .34 |
| Amplitude, ng/mL | .71 | .79 | .06 | .35 |
| Pulses/6h | 4.8 | 5.1 | .60 | .66 |
| Area under the curve | 374.0 | 344.9 | 44.1 | .65 |

[1]Standard error of least squares means, n = 16 cows.
[2]Observed significance level of least squares means.

Pulsatile luteinizing hormone (LH) measurements (amplitude, baseline, frequency, and pulses/6 hours), mean luteinizing hormone concentration, and area under the curve were similar (probability>0.33; as shown in Table 5) between control and insulin cows. This lack of luteinizing hormone responsiveness to insulin concentration agrees with Harrison and Randel (1986) who used beef heifers and with data reported by Beam and Holcombe (1992) in ewe lambs. The number of cows that showed estrual activity during the drylot period and that were pregnant after weaning was similar (probability>0.59; as shown in Table 6) between treatments. Although others have demonstrated an increase in ovulation rate in beef heifers (Harrison and Randel, 1986) and in gilts (Cox, et al., 1987) with administration of exogenous insulin, this treatment alone did not change any measurements related to reproduction for primiparous cows in thin body condition fed to maintain body weight.

TABLE 6

Estrus cyclicity at 120 d postpartum and fall pregnancy for primiparous cows administered s.c. injections of either saline (CON) or insulin (INS) Treatment

| Item | CON | INS | OSL[1] |
|---|---|---|---|
| Cyclicity | | | |
| Percent | 44.0 | 53.0 | .59 |
| Number of Cows | 7/16 | 8/15 | |
| Pregnancy | | | |
| Percent | 87.5 | 86.7 | .95 |
| Number of Cows | 14/16 | 13/15 | |

[1]Observed significance level of chi-square analysis.

Circulating insulin concentration in beef cows managed under a conservative nutritional regimen were successfully increased by administration of exogenous insulin. Furthermore, it appears that increased insulin may allow for energy storage in the form of improved body condition at the expense of milk production. An increase in insulin concentrations does not appear to be the sole regulatory mechanism of postpartum reproduction in primiparous beef cows.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, are hereby incorporated by reference.

What is claimed is:

1. A method of altering grazing animal blood constituents comprising the steps of:
   a) selecting a protein dietary supplement affecting the serum concentration of at least one blood constituent selected from the group consisting of serum insulin, serum urea nitrogen, serum glucose and serum growth hormone;
   b) administering the protein dietary supplement; and
   C) providing additional protein in the daily feed allotment while otherwise maintaining a negative energy diet.

2. The method of claim 1 wherein the step of selecting a protein dietary supplement further comprises the step of selecting a high rumen-degradable protein supplement.

3. The method of claim 2 wherein the step of selecting a high rumen-degradable protein supplement comprises the step of selecting cottonseed meal.

4. The method of claim 1 wherein the step of selecting a protein dietary supplement further comprises the step of selecting a low rumen-degradable protein supplement.

5. The method of claim 4 wherein the step of selecting a low rumen-degradable protein supplement comprises the step of selecting feather meal.

6. The method of claim 4 wherein the step of selecting a low rumen-degradable protein supplement comprises the step of selecting blood meal.

7. The method of claim 1 wherein the step of selecting a protein dietary supplement further comprises the step of selecting a protein dietary supplement selected from the group consisting of feather meal, cottonseed meal, blood meal and mixtures thereof.

8. The method of claim 1 wherein the step of selecting a protein dietary supplement further comprises the step of selecting feather meal.

9. The method of claim 1 wherein the step of selecting a protein dietary supplement further comprises the step of selecting cottonseed meal.

10. The method of claim 1 wherein the step of selecting a protein dietary supplement further comprises the step of selecting blood meal.

11. The method of claim 1 wherein the step of selecting a protein dietary supplement further comprises the step of selecting a mixture of blood meal and cottonseed meal.

12. The method of claim 1 wherein the step of selecting a protein dietary supplement further comprises the step of selecting a mixture of feather meal and cottonseed meal.

13. The method of claim 1 wherein the step of selecting a protein dietary supplement further comprises the step of selecting a mixture of blood meal and feather meal.

14. The method of claim 1 wherein the step of selecting a protein dietary supplement further comprises the step of selecting a mixture of cottonseed meal, feather meal and blood meal.

15. The method of claim 1, further comprising the steps of:
   selecting specific animal efficiency parameters in ruminants from the group consisting of body condition, body weight, milk production, reproduction and offspring weight; and
   administering said protein dietary supplement chosen to augment at least one of the selected specific animal efficiency parameters.

16. The method of claim 15 wherein the step of selecting specific animal efficiency parameters further comprises the step of selecting reproduction and offspring weight.

17. The method of claim 16 wherein the step of administering selected supplements further comprises the step of withholding protein supplements.

18. The method of claim 15 wherein the step of selecting specific animal efficiency parameters comprises the step of selecting decreased milk production.

* * * * *